United States Patent [19]
Hicks

[11] Patent Number: 5,387,195
[45] Date of Patent: Feb. 7, 1995

[54] NO SHARE SYRINGE

[76] Inventor: Charles D. Hicks, 326 Luna Dr., Nashville, Tenn. 37211-4131

[21] Appl. No.: 995,684

[22] Filed: Dec. 23, 1992

[51] Int. Cl.⁶ ............................................. A61M 5/00
[52] U.S. Cl. ................................... 604/110; 604/192; 604/264
[58] Field of Search ............... 604/110, 164, 165, 187, 604/218, 192, 195, 196, 263, 198, 191, 240, 194, 197, 213, 215, 236, 188; 128/917

[56] References Cited

U.S. PATENT DOCUMENTS

| | | | |
|---|---|---|---|
| 2,860,635 | 11/1958 | Wilburn | 604/207 X |
| 4,274,408 | 6/1981 | Nimrod | 604/165 |
| 4,488,545 | 12/1984 | Shen | 604/165 |
| 4,542,749 | 9/1985 | Caselgrandi et al. | 128/752 |
| 4,747,831 | 5/1988 | Kulli | 604/110 |
| 4,861,335 | 8/1989 | Reynolds | 604/88 |
| 4,915,699 | 4/1990 | Kornberg | 604/195 |
| 4,941,883 | 7/1990 | Venturini | 604/186 |
| 5,000,735 | 3/1991 | Whelan | 604/110 |
| 5,067,942 | 11/1991 | Jaffe et al. | 604/110 |
| 5,122,118 | 6/1992 | Haber et al. | 604/110 |
| 5,171,231 | 12/1992 | Heiliger | 604/263 |
| 5,221,266 | 6/1993 | Kastan | 604/192 |
| 5,224,936 | 7/1993 | Gallagher | 604/192 |
| 5,267,961 | 12/1993 | Shaw | 604/110 |
| 5,273,542 | 12/1993 | Blake, III | 604/110 |
| 5,279,593 | 1/1994 | Hiltebrandt | 604/264 |

FOREIGN PATENT DOCUMENTS

| | | | |
|---|---|---|---|
| 2632190 | 12/1989 | France | 604/110 |
| 3925834 | 2/1991 | Germany | 604/110 |

Primary Examiner—C. Fred Rosenbaum
Assistant Examiner—V. Alexander

[57] ABSTRACT

A truly single user syringe comprising means to put an end to the sharing of syringes, utilizing a combination of divided barrels having separate functions. One for the containment of bi-directional passage of fluids by way of a regulated valve means and elements relating thereto; and the other for the containment of fluids. This present invention uses a solid needle for pentration purposes and another means for the injection of fluids. This present invention is NOT USER FRIENDLY, uncompromising and cannot be shared.

1 Claim, 4 Drawing Sheets

NO SHARE SYRINGE

BACKGROUND OF THE INVENTION

Since their conception, hypodermic disposable syringes have been the mainstay of the drug abuser, due to their unrestricted accessibility.

The single most responsible entity in spreading communicable diseases, such as hepatitis "B" and the HIV virus causing AIDS has been the disposable syringe, the front-runner in spreading these diseases (by way of sharing the disposable syringes) into the heterosexual community. At this point in time, the heterosexuals are the front-runners in accelerating the spread of AIDS.

Recognizing the need for a more effective means of control to eliminate the spread of AIDS through the sharing of syringes, a more aggressive approach has been undertaken to design and patent disposable syringes, all claiming they are for one time use; incorporating devices such as needle shields, retractable needles, etc., some newly developed syringes, although effective in preventing reused by a needle trapping device within the needle shield, either by a movable retractable needle and/or a fixed needle, depending on a fixed or movable shield or by a plunger being disabled from a syringe stem function as claimed. Whatever method is used, the goal of the above described devices are for the purpose of disallowing further use of the needle.

Another earlier method of restricted use is that of disabling the plunger once loaded and fully depressed, incapable of refilling the syringe. In some cases the disabling ,of the plunger requires the full cooperation of the user in order to achieve its intended objective. Further and most noteworthy, having reviewed one time use, disposable syringes, is the fact these syringes can easily be tampered with, defeating their intended purpose, allowing for multiple use.

The above mentioned devices, all valiant in their attempts at preventing the sharing of syringes, encourage rather than discourage the sharing of syringes. A user abuser using a syringe he knows will become useless once the contents of the syringe has been expelled, (requiring 25 units of fluid) will fill the syringe to its maximum amount, (100 units) for the purpose of reusing the syringe for multiple sharing.

All the present so called (one time use) disposable syringes patented today claim one use. They all function as claimed, however, they do not STOP the user from withdrawing the needle from himself during the time of injection, allowing other users to repeat the same act, permitting sharing of the syringe contents multiple times. Considering all the above, there is a great need for a TRULY one time user disposable syringe, from a single user and once withdrawn from the flesh of a single user, rendered useless, regardless of the contents remaining within the syringe. Further, any attempts to tamper with its intended function is impossible, since to defeat any one of the three cooperatively dependent mechanisms, will prematurely disable the syringe..

This present, TRULY one time single user, disposable syringe is a great need, both in the United States of America and in the World.

SUMMARY OF THE INVENTION

The invention as presented is to provide a truly one time single user disposable syringe. In this present invention are cooperative means, a solid slideable needle, an (in place) intravenous tube, and a (bi-directional), fluid passage valve assembly, to allow for one time Insertion filling, and withdrawal from a fluid source, and one time injection, into the flesh of a single user and one time withdrawal from a single user, whereupon the syringe as set forth is rendered useless; regardless of the remaining contents within the syringe. Further, this invention as presented provides protection from accidental needle strikes by a possible contaminated needle, since the needle is contained within the syringe at such times accidental sticking could occur.

This present invention also provides a fluid opening and closing valve within the fluid passage valve assembly allowing and restricting the flow of fluids into and/or out of the fluid containment chamber, working cooperatively with other mechanisms to accomplish the above.

DETAILED DESCRIPTION OF THE DRAWINGS

Figure 1:
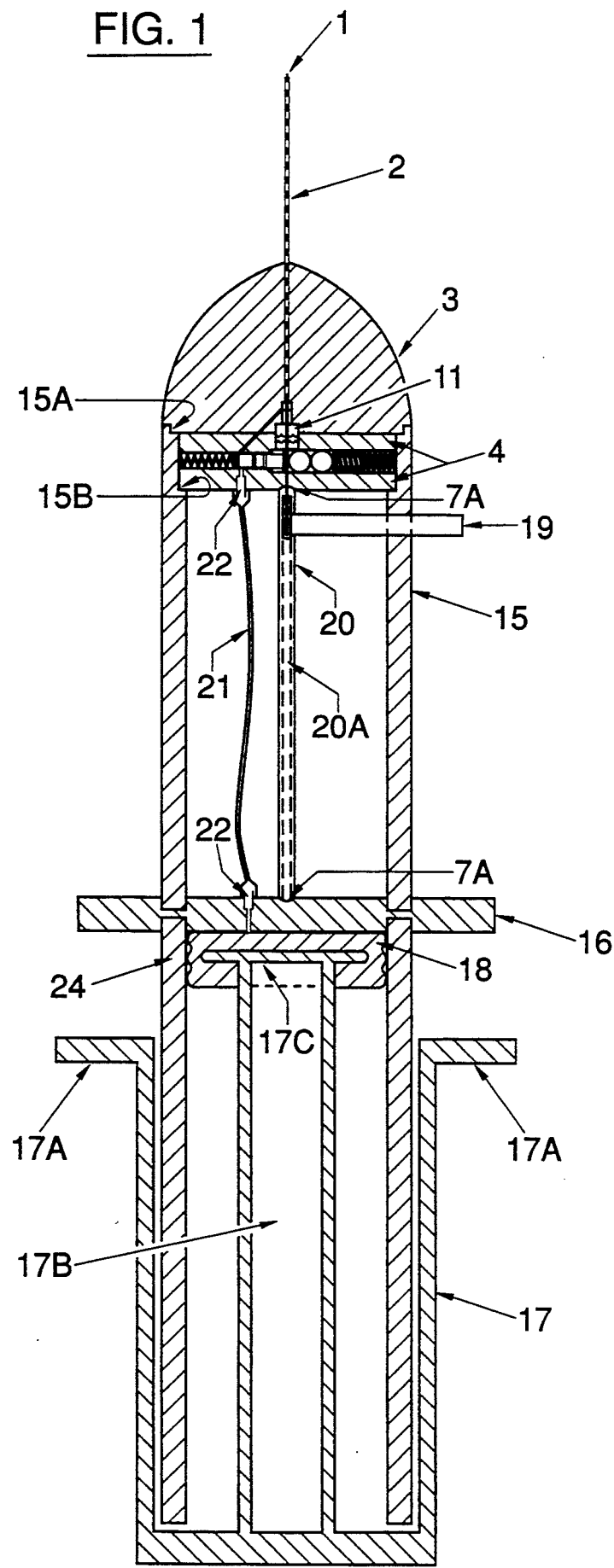
FIG. 1 is a full longitudinal cross-section view of the present invention.

FIG. 1 shows a full longitudinal cross-section view of the cylindrical syringe as presented to the consumer, ready for use. Certain embodiments shown in FIG. 1 are not described and/or not identified in order to avoid clutter within the drawing, and are found, detailed in specifications that follow.

The largest structures making up the cylindrical syringe body are the forward syringe barrel 15 and the aft syringe barrel 24.

Also show is the plunger assembly 17, being an elongated cylindrical barrel 17, of one piece rigid construction with an inner cylindrical bore whose inner circumference provides for a semi loose fit over the near full length of the aft syringe barrel 24.

Projecting outwardly out of plunger assembly 17, at its near forward most end, are stems 17A, serving as finger holds, whose outer most extension slightly exceeds that of the aforementioned finger holds of the barrels coupling device 16. Also shown and diametrically centered is the plunger shaft 17B, projecting out of its cast in place central location in the plunger assembly 17, aft most closed end, being of a cylindrical hollow construction whose forward most end is located, the plunger shaft 17B, plunger shaft endcap 17C, a circular, flat, cast in place outward extension of the plunger shaft 17B, with a central hole corresponding to the inner circumference of the plunger shaft 17B, whereupon, plunger endcap 17C, is installed a plunger 1,8. Plunger 18 is composed of a suitable rubber or plastic material having an inner centrally located slot to allow firm fixation onto plunger endcap 17C. As shown the aft end of the aft barrel 24 is open, since the plunger 18 and plunger assembly 17 can be removed from the open end of the aft syringe barrel at any time.

NOTE: Although plunger assembly 17 is pointed (in FIG. 1 ) at the cylindrical barrel of the plunger assembly 17, it could as well point to any described feature of the plunger assembly 17. All that is described to be the plunger assembly 17, i.e., 17A, 17B and 17C, are all of one piece construction, excluding the plunger 18.

Figure 2:
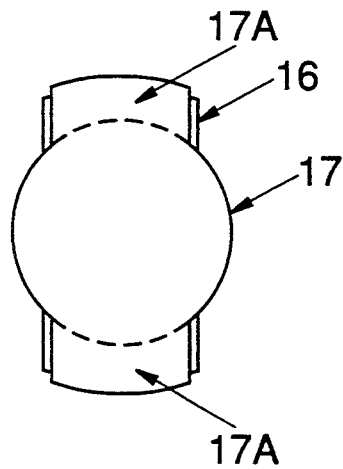
FIG. 2 is a rear view of this invention, as presented.

FIG. 2 shows a vertical rear view of the present invention. 17 is the outer body of the plunger assembly. No. 17A are the outer extending finger holds of the barrels coupling device 16, serving as finger holds.

Figure 3:
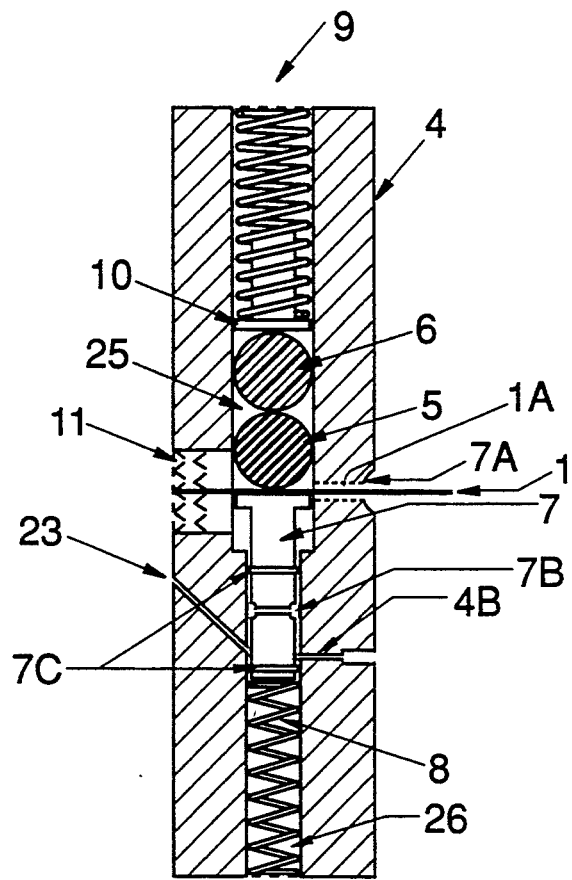
FIG. 3 is a full longitudinal cross-section view of the fluids passage valve assembly 4 and its components as it appears assembled.

FIG. 3 shows a longitudinal cross-section view of the fluid passage valve assembly 4, presented in the invention. Fluid passage valve assembly 4 is circular in dimension, composed of a suitable rigid material and has a diametrically, laterally centered bored hole 3A in which is housed the aft end of the rubber ball housing 11, (See FIGS. 18 and 13). The forward end of the rubber ball housing 11 is housed within the aft end of the syringe endcap 3, in bored hole 3A. While passing laterally through the exact center of the fluid passage valve assembly 4 aft wall is bored hole 1A, of an inner cylindrical bore slightly larger than the solid needle 1 which passes forward and aft at the location. However, when solid needle 1 cannot be withdrawn beyond the middle of the aft wall 41 of the fluid passage valve assembly 4, which is slightly larger.

That which is represented in FIG. 3 is the fully assembled fluid passage valve assembly 4, except for the attachments of the coupling device 22, in which all the components therein are housed. The upper bored hole 25 is shown centrally located at the top of the cylindrical shaped fluid passage valve assembly 4, and is bored downwardly through and past the central most part of the fluid passage valve assembly 4 to a precisely calibrated location where at the location upper bored hole 25 graduates in inner bore size creating lower bored hole 26 which continues downwardly through the fluid passage valve assembly 4, leaving both ends prior to assembly. With the exception of spring 8, inserted into the lower bored hole 26 of the fluid passage valve assembly 4, all components of the fluid passage valve assembly 4, are inserted through the upper bored hole 25, and in the following order. The lower stem 7, cylindrical in shape, being of one piece rigid construction, has its uppermost end an increase in stem circumference, slightly less than the inner circumference of upper bored hole 25. This increase in thickness and circumference of the lower stem 7 uppermost end prohibits its entry into the lower bored hole 26. The narrow and longer end of the lower stem 7 is inserted, narrow end first where it rests upon the top of lower spring 8. The lower stem 7, shown resume ,containing two cylindrical grooves for the installation of two "O" rings 7C, serving as fluid back flow preventors, composed of a rubber or like material capable of preventing leakage of any fluids beyond their locations above and below fluid passage groove 7B. Once the lower stem 7, is in place, the solid needle 1, is inserted thru the aft centrally located bored hole 1, in the fluid passage valve assembly 4, aft wall, restricting movement of the lower stem 7 beyond the lower side of solid needle. Next to be inserted is a rubber ball 5, of a density to allow needle 1, penetration and forward rubber ball 5 movement into the rubber ball housing 11. The rubber ball 5 is shown resting against solid needle 1. The next element inserted is a rigid plastic ball 6, followed by a cylindrical cap 10, whose forward cylindrical end is sized to move easily within the larger cylindrical bore 25, whose aft stem end also 10, having a reduced outer circumference to fit snugly within the forward end of spring 9, the last element to be inserted into the upper cylindrical bore 25.

Figure 3A:
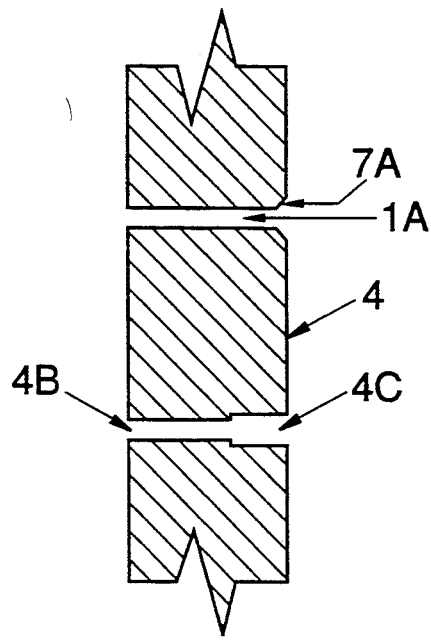
FIG. 3A is a partial exploded cross-section view of the aft wall of the fluid passage valve assembly 4. The upper most bored hole 1 A, houses the forward most point of the needle when in its fully retracted near mid location inside the aft wall of the fluid passage valve assembly 4. The lower bored hole 4C provides for the bi-directional regulated flow of fluid passage valve assembly 4 and the attachment of a coupling device 4B, which increase in bore size located in the aft most end of FIG. 3A.

FIG. 3A shows an exploded partial cross-section vertical view of a cylindrical bored hole with an inner reduction in bore size, located within the lower aft section of the fluid passage valve assembly 4, the bored hole 4B, serving as a fluid passage hole and the aft larger bored hole 4C serving to house the connector tube 22, also shown in FIG. 1.

Figure 3B:
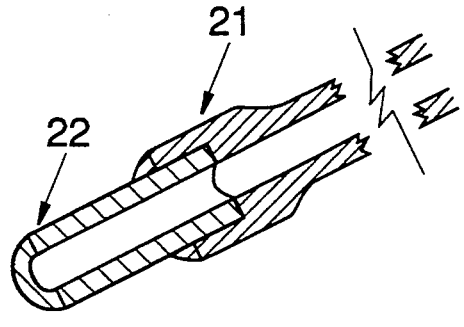
FIG. 3B is a cross section view of the fluid passage tube coupling device, coupled to the fluid passage tube, 21.

FIG. 3B shows a partial horizontal cross-section view of the fluid passage tube 21, mounted on the connector tube 22, and its fluid passage tube 21.

Figure 4:
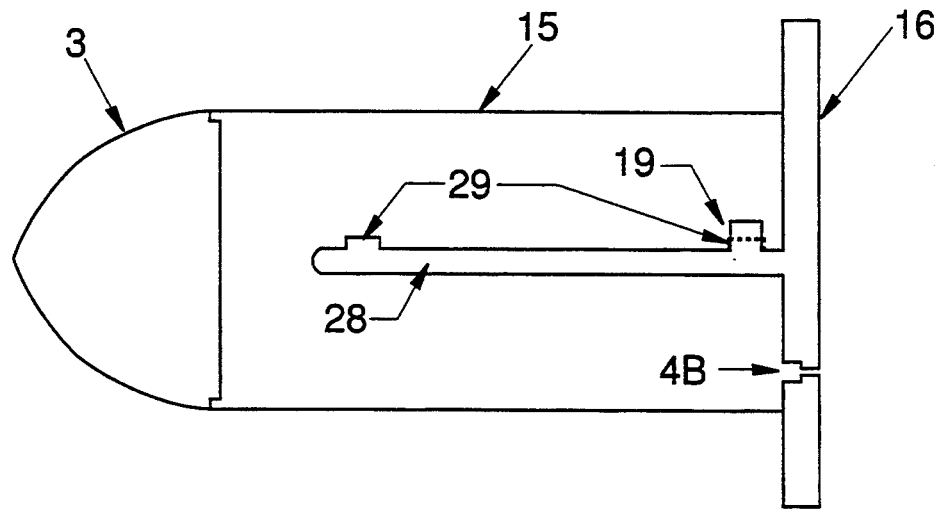
FIG. 4 is a schematic top view of the forward barrel of the syringe also showing the syringe endcap and the barrels coupling device attached. Also shown is the forward syringe barrel, slot 28 out of which projects the needle slide stem A, shown projecting above the forward syringe barrel slot 28 and locked in the aft stem lock 29.

FIG. 4 shows a general schematic horizontal view of the forward syringe barrel 15, slot 28, running through its upper cylindrical wall from the aft end of the forward syringe barrel 15, its near full length, out of which projects the needle slide stem 19. During the course of operating the syringe toward accomplishing its intended function, that of inserting and withdrawing the solid needle 1, in and out of the intravenous tube 2, the aft end of solid needle 1, being fused in the lower end of the needle slide stem 19, is advanced forward and aft with the syringe barrel slot 28. Needle slide stem 19 must be locked in aft stem lock 29, in order to open the fluid passage valve assembly 4, allowing for the bi-directional flow of fluids into and out of the aft syringe barrel 24. Syringe endcap 3, illustrates how the forward syringe barrel 15, is closed and barrels coupling device 16, shows how the aft end of the forward syringe barrel 15, is closed. (See FIG. 1.)

Figure 5:
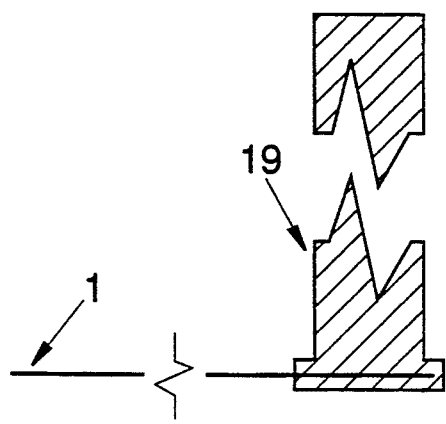
FIG. 5 is an exploded cross-section view of the needle slide stem 19 of the present invention.

FIG. 5 shows a vertical cross-section view of the needle slide stem 19, and the fused attachment of the aft end of solid needle 1.

Figure 6:
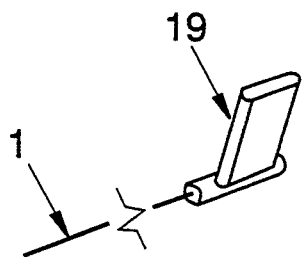
FIG. 6 is a top oblique view of the needle slide stem 19 of the present invention.

FIG. 6 shows a combination view of the needle slide stem 19, and the solid needle 1, projecting outwardly from the needle slide stem 19, lower end. The lower most end of the needle slide stem 19, is round in shape, allowing for a smooth fit within the inner cylindrical base of the needle slide stem housing 20. The needle slide stem slot 20A, is also slightly wider than the width of the needle slide stem 19, in order to allow ease of movement.

Figure 7:
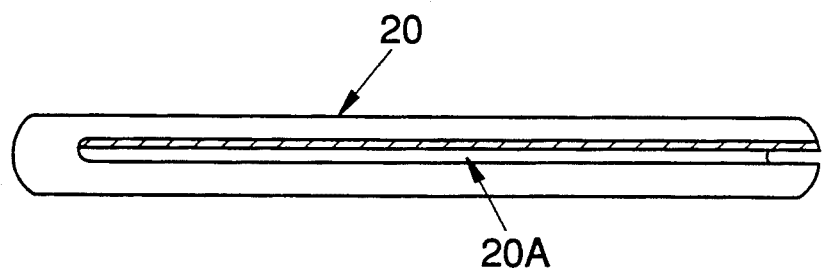
FIG. 7 is a horizontal top view of the needle slide housing 20, and 20A, of the present invention.

FIG. 7 shows the needle slide stem housing 20, being open at both ends and the needle slide stem slot readied for the insertion of the needle slide stem 19, thru the aft end of the needle slide stem housing 20. Both ends of the needle slide stem housing 20, are rounded for ease of movement, (clockwise and counted clockwise) when installed within their respective levels 7A; bring the aft wall of the fluid passage valve assembly 4, and the forward wall of the barrels coupling device 16. Once installed the aft end of the needle slide stem slot 20A, is calibrated to be in direct alignment with the forward stem lock 29, when needle slide stem is in its forward most position.

Figure 8:
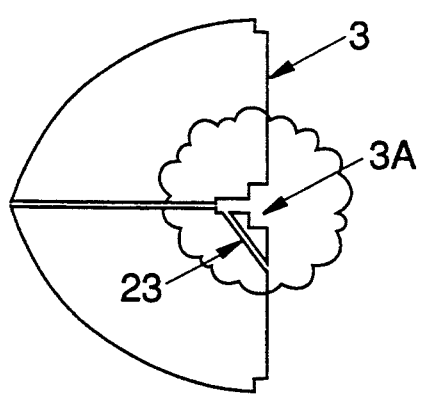
FIG. 8 is a side view of the bored holes in the syringe endcap showing the reduction of bore size of the present invention.

FIG. 8 shows a side profile view of the bored holes within the syringe endcap 3, with a clouded emphasis on bored hole 3A, is a cylindrical bore, centrally located within the syringe endcap 3, and is twice reduced in inner bored size circumference. Also shown is an upward diagonally bored hole 23. (See FIG. 10 for a detailed reference).

Figure 9:
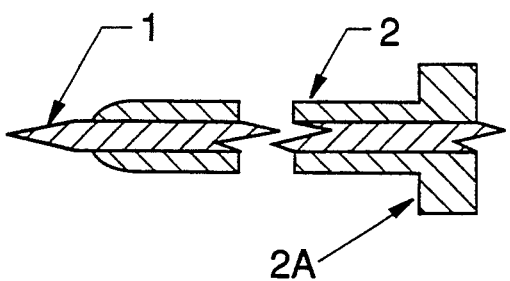
FIG. 9 is an exploded cross-section view showing the needle assembly of the present invention.

FIG. 9 shows horizontal cross-section view of the solid needle 1, encompassed by the intravenous tube 2, which is composed of a very flexible material and is housed within the syringe endcap, projecting an adequate distance beyond the syringe near the full length of the solid needle 1, which when positioned in its forward stem lock 29, extends a slight distance beyond the forward most end of intravenous tube 2. The solid needle 1, is composed of a rigid plastic or metal material and since a hollow bore in solid needle is not necessary, the Solid needle approximates the outer circumference of a typical hollow needle when combined with the intravenous tube 2.

Figure 10:
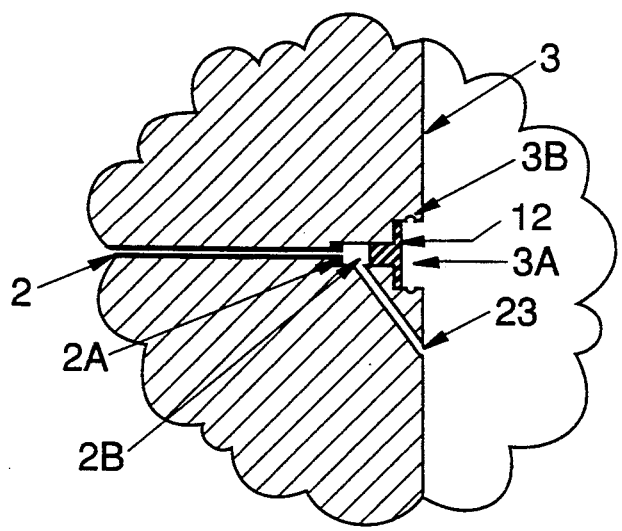
FIG. 10 is an exploded detailed view of the clouded area of FIG. 8 of the syringe endcap of the present invention.

FIG. 10 shows an exploded view of the clouded area in FIG. 8 showing occupancy of the components housed therein. The intravenous tube 2, is inserted into bored hole 3A, and into the second graduation in inner bore size of 3A, which is bored hole 1A, where it continues through bored hole 1A, the near length of solid needle 1. The forward most aft end of the intravenous tube 2, (See FIG. 9 and 10) is fused onto the wall of the first reduction in bore size of bored hole 3A. The backflow gasket 12, composed of material suitable in density to prevent backflow absorbtion of fluids beyond its forward most location, while allowing solid needle 1, ease of penetration. The forward most cylindrical end of the backflow gasket 12, extends approximately half the forward distance of the first reduction in bored hole 3A, having the aft cylindrical end of the backflow gasket 12, firmly seated to the forward wall of the forward most bored hole 3A, preventing forward and/or movement of the backflow gasket 12. Also shown within the larger bored hole 3A, is an outwardly extending cylindrical groove 3B, an inner cylindrical groove within bored hole 3A, which houses another component to be installed, shown in detail in FIG. 13. The hollow area shown between locations 2A, and the forward most end of the backflow gasket 12, serves as a fluid basin 2B, being diagonally intersected at its forward most end by the diagonally bored hole 23 serving as a fluid passageway thru the syringe endcap 3.

Figure 11:
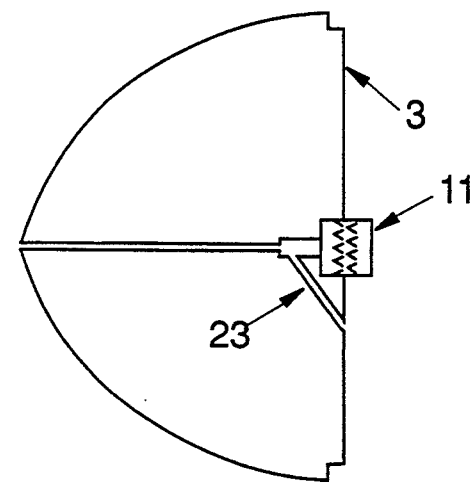
FIG. 11 is a schematic view of the syringe endcap.

FIG. 11 is a schematic, partial side view illustrating the location of the last component to be inserted into the syringe encap 3, the rubber ball housing 11, composed of a suitable metalic material. Also illustrating that portion of the rubber ball 2, housing 11, that is housed within the syringe endcap 3.

Figure 12:
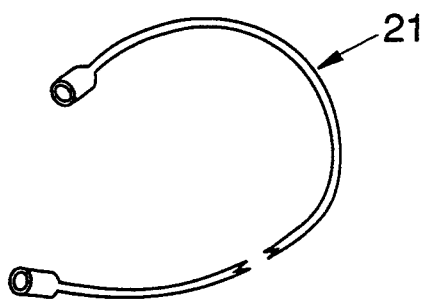
FIG. 12 is a view of the fluid passage tube of the present invention.

FIG. 12 shows a partial view of the fluid passage tube 21, whose oversized ends couple to that part of the connector tubes 22, when located within the forward syringe barrel 15, (See FIG. 1.) The fluid passage tube allows for the bi-directional flow of fluids thru forward syringe barrel 15, and for filling, clearing and discharging of fluids into and out of the aft syringe barrel 24.

Figure 13:
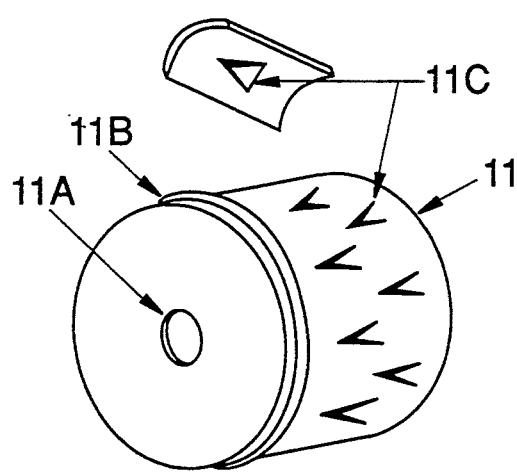
FIG. 13 is an oblique top and side view of the rubber ball housing of the present invention.

FIG. 13 shows a semi oblige front and aft, top and side view of the rubber ball housing 11. Rubber ball housing 11 is a cylindrical hollow barrel of an elongated length composed of a suitable metal material to securely house and trap the rubber ball 5 when moved forward into the rubber ball housing 11, due to the advancement of the solid needle 1. The rubber ball housing 11 has two off center cylindrical rows of sharp inwardly projecting barbs 11 C, triangular in shape allowing entry of the rubberball 5, while restricting its backward movement, since withdrawal of solid needle 1, from its location within a fluid source causes the rubber ball 5 to be pierced by the sharp barbs 11C trapping the rubber ball 5 inside the rubber ball housing 11. Also shown is a centrally located hole 11A located in the otherwise closed forward end of the rubber housing 11 allowing adequate room for the solid needle 1 to pass through. The rubber ball housing 11 is the last component to be inserted into the syringe endcap 3 when the outwardly extending cylindrical depression 11B located near the forward end of the rubber ball housing 11 is snapped in place in the corresponding bored hole, outwardly extending, cylindrical groove 3B, located within No. 3A of the syringe endcap 3, the rubber ball housing 11 is then immovable and the part of the rubber ball housing 11 shown extending beyond the syringe endcap 3 is inserted in the centrally located cylindrical bore in the forward wall 4, of the fluid passage valve assembly 4.

NOTE: The forward end of the rubber ball housing 11 tightly fits against the corresponding shape of the aft end of the back-flow gasket 12, prohibiting forward or aft movement of the back-flow gasket 12.

Once all components are assembled, ready for use as shown in FIG. 1, RE: FIG. 4, 29 and FIG. 3A the following mechanics come into play. The solid needle 1 and intravenous tube 2 are inserted into a fluid source for withdrawal of fluids into the syringe, which is impossible since the intravenous tube 2 is occupied by the solid needle 1 and the lower stem 7 is closed preventing the flow of fluids through the fluid passage valve assembly and into the aft syringe barrel 24. The solid needle 1 must be withdrawn from the intravenous tube 2, while the intravenous tube remains in the fluid source. This is accomplished by unlocking the needle slide stem 19 from its forward stem lock 29 and sliding the needle slide stem 19 backward, locking it in the aft stem lock 29. Note: the syringe is operable only when the needle slide stem 19 is locked in the critical locations in the stem locks 29. The rubber ball 5 that rested against the solid needle 1, upon pressure from the upper spring 9 moves into its calibrated central location within the lower cylindrical bore 25, once withdrawal of the solid needle 1 has been removed from the intravenous which remains in the fluid source has taken place. At this time the tip of the solid needle 1 resides at it's calibrated central location in the center of the aft wall in bored hole 1A of the fluid passage valve assembly see FIG. 3.

Note: The needle slide stem 19 is locked in the aft stem lock 29. The downward movement of the rubber ball 5 is illustrated in FIG. 3 is exactly the radius of the rubber ball 5 whose downward movement causes the lower stem for 7 to move downwardly, exactly the radius of the rubber ball 5 whose downward movement is restricted by the upper cylindrical end of the fluid passage valve 7, located in the upper cylindrical bore 25, comes into contact with the reduction of inner cylindrical bore size of the lower bore 25 at location 26. At this point the fluid passage valve overflow 7B is brought into direct alignment lower with the diagonally bored hole 23, and bored hole 4B, located in the lower fluid wall of the fluid passage valve assembly 4. At this point in time the fluid is able to pass thru fluid passage tube 21, and into coupling device 22 and thru the fluid passage way 23 also located in the barrels coupling device 16 and into the aft barrel 24.

The intravenous tube 2 is now removed from the fluid source. The syringe is now ready for filling. This is accomplished by withdrawing the plunger assembly 17, and filling the aft syringe barrel 24 past it's desired amount to allow for clearing. At this point the user cannot insert the very flexible intravenous tube into his flesh, he must first insert the solid needle 1 into the intravenous tube 2. This is accomplished by unlocking the needle slide stem 19 from its aft stem lock location 29 and advancing it forward into it's forward stem lock 29 location. Prior to this activity the point of the solid needle 1 was housed midway within the bored hole 1,1 A, in the fluid passage valve assembly 4. As the solid needle 1 is advanced forward, the point of the solid needle 1 comes into direct central contact with the rubber ball 5, advancing the rubber ball 5 forward into the rubber ball housing 11, advancing rubber ball 5 by way of penetrating it as the solid needle 1 is advanced further through the back-flow gasket 12 and into and thru intravenous tube 2 to its most forward and is locked in fluid stem lock 29. The solid needle 1 and intravenous tube 2 are now ready for penetration into the flesh of the user location extending slightly beyond the intravenous tube 2. During the course of this activity the forward displacement of the rubber ball 5 allows for the plastic ball 6 under pressure from spring 9 to come to rest against the solid needle 1, at the time of the process the lower stem is also advanced, under pressure from lower spring 8 to come to rest on the lower side of solid needle 1, interrupting the flow of fluids. (see FIG. 3). The fluid passage Valve assembly 4 is now closed.

The solid needle 1 and intravenous tube 2 are now ready to be inserted into the flesh of the user. After user injection, and in order to expel the fluid contents in the aft barrel 24, solid needle 1 must again be removed from its forward stem lock 29 and relocated in the aft stem lock 29, the fluid passage valve assembly 4 is now open. While in the course of withdrawing solid needle the intravenous tube 2 remains in the flesh of the user, the withdrawal of the solid needle 1 forces the rubber ball 5 into the sharp barbs FIG. 13, 11C, trapping the rubber ball 5 within the rubber ball housing 11. As the solid needle 1 passes the plastic ball 6 it is forced under pressure from upper spring 9 into the former central location vacated by rubber ball 5, forcing the opening of the alignment for the passage of fluid from valve stem 7, duplicating the previously mentioned fluid source. The fluids are now able to be expelled from the aft barrel 24 into the flesh of the user by the forward movement of the plunger assembly 17, using the finger holds of the barrels coupling device 16 and the finger holds 17A of the plunger assembly 17. Any attempt during the expulsion of fluids to remove the intravenous tube 2 from the user for further use (e.g. sharing) of the syringe is impossible, since the intravenous tube 2 cannot be inserted into the flesh, also the solid needle 1, required for penetration is trapped behind the plastic ball 6 which is trapped behind rubber ball 5. Note: spring 8 is of a much lesser resistance than that of spring 9. Spring 8 serves to close the valve stem 7, when solid needle 1 is in its forward most position and centrally occupies bored hole 3A, allowing an override by spring 9, opening the fluid passage valve assembly 4, allowing the expulsion of fluids from the aft syringe barrel 24, into the user.

Note: Any and all references made regarding locking solid needle 1 in stem locks 29 and the advancing and withdrawing of solid needle 1 are and were accomplished by the use of that part of needle slide stem 19 that projects out of the forward syringe barrel 15.

METHOD OF ASSEMBLY

The intravenous tube 2 is inserted into the syringe endcap 3, through the bored hole 3A, where its forward most elongated end enters the second graduation in bore size of bored hole 3A. Intravenous tube 2 then is moved through and beyond the outermost forward end of the syringe endcap 3 a calibrated distance, just shy of the solid needle 1 upon its forward most extension. See FIG. 1. At this point in time, the forward most aft end 2A of the intravenous tube 2 is fused to the front cylindrical wall of the first reduction of bore size of bored hole 3A.

The next component to be inserted into the syringe endcap 3 is the backflow gasket 12, its cylindrically narrower forward end (once fully inserted into the first graduation of inner bore size of bored hole 3A) falls just short of the diagonally bored hold 23, creating a fluid basin 2B, between the forward end of the backflow gasket 12 and the aft end of the intravenous tube 2. (See FIG. 10.)

The next component to be inserted into the syringe endcap is the rubber ball housing 11. Rubber ball housing 11 has at its forward end an outwardly stamped cylindrical ring 11B, which fully encompasses its upper cylindrical barrel, corresponding cylindrical groove 3B in the bored hole 3A. Once rubber ball housing 11 is inserted into bored hole 3A, cylindrical groove 3B and outwardly stamped cylindrical ring 11B, snap in place, tightly securing the rubber ball housing 11 from any forward or aft movement. The front face of rubber ball housing 11 also fits tightly against the aft end of the backflow gasket 12, anchoring it in place, also prohibiting forward or aft movement of the backflow gasket 12. The assembly of the fluid passage valve assembly 4 as previously described did not go into detail when mention of the insertion of solid needle 1 due to the complexity of installation, which is described as follows: The coupling device 22 is inserted in bored hole 4C located in the aft wall of the fluid passage valve assembly. Onto that part of coupling device 22 which extends inwardly into the forward syringe barrel 15. The exploded end of fluid passage tube 21 is attached.

The solid needle 1 must be inserted into the needle slide stem housing 20 with the needle slide stem projecting through the needle slide stem slot 20A and further projecting through and beyond the syringe barrel slot 28 located in the forward syringe barrel 15. While advancing solid needle 1 forward; keep in mind the syringe, the end cap 3 and the fluid passage valve assembly 4 remain unattached, and at this time the only two components having been installed in the fluid passage valve assembly 4 are the lower spring 8 and the lower stem 7. Allowing the lower spring 8 to slightly ease out of its location in lower bored hole 26 and further provides the lower stem 7 downward movement; thus allowing the advancement of solid needle 1 to a location midway within the syringe endcap 3. At this point in time the other components above solid needle 1 (as described on page 8, lines 18 (and continuing) through the installation of upper spring 9. At this point in time the fluid passage valve assembly 4 is inserted and fused into inner cylindrical bore 15B. The syringe endcap 3 can then be moved downward and positioned so as to bring into perfect alignment, diagonally bored hole 23 and bored hole 4B (see FIG. 3); the cylindrical groove shown in the aft end of the syringe endcap 3 (see drawings, FIG. 4, FIG. 8, and FIG. 11 ) can then be fused into its location, inner cylindrical bore 15A.

The coupling device 22 is now inserted into bored hole 4C in the forward wall of the barrels coupling device 16, and onto that portion which remains inside the forward syringe barrel, the exploded aft end of the fluid passage tube 4 is firmly attached. After this process, the forward and aft ends of the needle slide housing 20 located in their inner bevels 7A (by manipulation of needle slide stem 19) and the barrels coupling 16 inner cylindrical groove 3B is fused onto the aft end of the forward syringe barrel 15. The needle slide stem 19 is now advanced to its forward most position in the syringe barrel slot and locked in forward stem lock 29.

The previously mentioned forward syringe barrel 15 forward and aft open ends are now closed, as well as the aft end of the needle slide stem housing 20, the needle slide stem slot 20A, and the syringe barrel slot 28.

The plunger 18 is now fitted onto the plunger shaft endcap 17C and the plunger assembly 17 is fitted into and around the aft syringe barrel 24. The forward end of the aft syringe barrel 15 is now ready to be inserted and fused into the inner cylindrical groove in the aft wall of the barrels coupling device 16. The aft end of the aft syringe barrel is considered open since the plunger assembly can be withdrawn at anytime.

I claim:

1. A one time use disposable syringe where said syringe is incapable of further use once said syringe is removed from a patent comprising:
    a pair of elongated cylindrical barrels each having an interior cylindrical bore said barrels each being composed of a suitable rigid material where said barrels are defined sectionally as a forward and are aft barrel;
    a cylindrical insert within said barrels composed of a rigid material and which seals said forward and said aft barrels together at one end and includes a fluid passage tube which extends within said forward barrel;
    said aft barrel including a plunger assembly composed of rigid material having an inner bore located centrally within an elongated barrel with a circumference which is larger than that of said aft barrel allowing for a semiloose fit over said aft barrel with are outward extension at a forward end of said plunger assembly of an adequate size to serve as finger holds, a plunger shaft centrally located within said plunger barrel having at, endcap, and a common syringe plunger having an inner slot corresponding to said endcap which is instrumental in providing filling, clearing and discharging fluids through said syringe;
    said forward barrel including a rigid syringe endcap at an end opposite end where said aft and said forward barrels are sealed through which fluid passes and includes a means for controlling fluid flow;
    a fluid passage assembly which includes a valve and a progressively cooperative means contained within said forward barrel where said cooperative means controls the opening and closing of said valve allowing for one time bi-directional flow of fluid into said aft barrel and a one time partial of full discharge of said fluid from said aft barrel; and
    a needle assembly means within said syringe endcap including a needle composed of rigid or flexible material and where said means provides a one time penetration into and one time withdrawal from the patient by sliding said needle into and out of said forward barrel when said valve is open or closed, respectively.

* * * * *